United States Patent [19]

Mitchnick et al.

[11] Patent Number: 5,562,897
[45] Date of Patent: Oct. 8, 1996

[54] METHOD OF PROTECTING THE SKIN

[75] Inventors: Mark Mitchnick, Wainscott, N.Y.; Anthony J. O'Lenick, Jr., Lilburn, Ga.

[73] Assignees: Siltech Inc., Norcross, Ga.; SunSmart Inc., Wainscott, N.Y.

[21] Appl. No.: 629,931

[22] Filed: Apr. 12, 1996

Related U.S. Application Data

[63] Continuation-in-part of Ser. No. 549,873, Oct. 30, 1995, Pat. No. 5,536,492, which is a continuation-in-part of Ser. No. 490,494, Jun. 14, 1995, Pat. No. 5,486,631.

[51] Int. Cl.$^6$ .............................. A61K 7/42; C07F 7/08; C07F 7/28
[52] U.S. Cl. .................................. 424/59; 556/10
[58] Field of Search ......................... 424/59; 556/10

[56] References Cited

U.S. PATENT DOCUMENTS

| | | | |
|---|---|---|---|
| 3,418,347 | 12/1968 | Levene | 556/10 |
| 3,461,146 | 8/1969 | Turner et al. | 556/10 |
| 3,758,535 | 9/1973 | Vizurraga | 556/10 |
| 4,122,062 | 10/1978 | Monte et al. | 556/10 X |
| 4,157,978 | 6/1979 | Llenado | 556/10 X |
| 5,340,567 | 8/1994 | Cole et al. | 424/59 |
| 5,468,471 | 11/1995 | Zecchino et al. | 424/59 |
| 5,476,643 | 12/1995 | Fogel | 424/59 X |
| 5,486,631 | 1/1996 | Mitchnick et al. | 556/10 |
| 5,498,406 | 3/1996 | Nearn et al. | 424/59 |

*Primary Examiner*—Paul F. Shaver

[57] ABSTRACT

A process for protecting skin with a hydrophobized titanium dioxide is disclosed. The silicone composition is prepared by the reaction of a reactive alkoxy silicone which is applied to the titanium dioxide then in a subsequent step the coated titanium dioxide is heated to 40 to 100 C. for between 1 and 10 hours for the reaction to occur. The resulting titanium dioxide which is hydrophobic, non-reactive, and not affected by water, is applied to the skin for protection from Ultra violet light of the sun.

20 Claims, No Drawings

METHOD OF PROTECTING THE SKIN

RELATED APPLICATIONS

This application is a continuation in part of Ser. No. 549,873, now U.S. Pat. No. 5,536,492 filed Oct. 30, 1995, which is a continuation in part of Ser. No. 490,494 filed Jun. 14, 1995, now U.S. Pat. No. 5,486,631.

This invention relates to a process for protecting skin with a hydrophobized titanium dioxide is disclosed. The silicone composition is prepared by the reaction of a reactive alkoxy silicone which is applied to the titanium dioxide then in a subsequent step the coated titanium dioxide is heated to 40 to 100 C. for between 1 and 10 hours for the reaction to occur. The resulting titanium dioxide which is hydrophobic, non-reactive, and not affected by water, is applied to the skin for protection from U.V.

Compositions made according to the invention are very effective as delivery systems which produce uniform hydrophobic film which are not interrupted by extraneous oils, water and other additives which may be in the final formulated product. The titanium dioxide modified by this process results in a more chemically inert particle.

DESCRIPTION OF THE ART

Titanium dioxide is a well known material useful in a variety of applications. It is used as a pigment in paint, as an additive in cosmetic products, cements, glass, rubber, glue, matches, inks and semiconductors. The use of titanium dioxide in so many applications areas is a direct result of the many differing properties of the pigment.

It is very desirable to produce a titanium dioxide which has the pigment properties but lacks the reactivity found in untreated titanium dioxide.

One area in which titanium dioxide has been used is in sun screen products. It protects the skin from sun. The traditional materials used for protecting the skin from the harmful effect of the sun are the organic sun screens. These include para amino benzoic acid and other materials which absorb ultra violet light. Recently, studies have indicated that ultra violet light is a major factor in the ageing of skin. This has resulted in the incorporation of sun screens in products which are not aimed specifically for use at the beach, like make up. Additionally, there has been an increased interest in providing higher levels of protection to the skin. The so called SPF system has been developed to evaluate various materials for their effectiveness in protecting the skin from the damaging affects of the sun. The quest for higher and higher SPF values has resulted in the use of greater levels of organic sun screen. These materials have a tendency to be irritating at high concentrations, and have the affect of increasing the available organic material for bacteria. This results in the need for more preservative to protect the higher level of organic sun screen agent from bacterial degradation. The higher levels of preservative result in higher irritation levels, which can be addressed by incorporation of irritation mitigants, which themselves are degraded by bacteria.

The use of inorganic sun screen agents like titanium dioxide is a good way around the use of organic sun screens, since they are not attacked by bacteria. However, their use does have some other inherent problems. Specifically, these materials are not easily formulated into stable products, due to the reactivity issues raised above. titanium dioxide tends to agglomerate in many finished formulations, loosing it's effectiveness in the formulation and resulting in unacceptable aesthetic results, most commonly whitening and viscosity changes. In addition, untreated $TiO_2$ reacts with vitamin C in aqueous solution, resulting in a pronounced yellowing of the solution. This is highly undesirable in many cosmetic applications.

One approach has been to pre-disperse the titanium dioxide in an organic oil like Siltech's patented tri-(octyldodecyl)-citrate. While the dispersion is fairly stable, the coating is not permanent since there is no reaction between the oil and the titanium dioxide. The oil also disrupts the uniformity of the titanium dioxide on the skin. Traditionally, dispersing aids have been added to formulations to minimize the disruptive effect upon the film. These include phosphate esters, and lecithin. These too suffer from the labile nature of the surface treatment and dissociation between the particle and the oil. This is especially evident when titanium dioxide is exposed to extreme mechanical or thermal stress as in the production of plastics or stick cosmetics.

The present invention overcomes the shortfalls of titanium dioxide by reacting a specific silicone compound under controlled conditions to produce a stable, surface treated titanium dioxide which maintains it's state of dispersion and does not contribute significantly to chemical instability in the formulation.

SUMMARY OF THE INVENTION

The present invention discloses (a) a process for hydrophobizing the surface of titanium dioxide with a specific type of reactive silicone, and (b) a novel hydrophobic titanium dioxide composition.

DETAILED DESCRIPTION OF THE INVENTION

It has been found that highly effective system for hydrophobizing titanium dioxide makes use of a silicone compound conforming to the following structure:

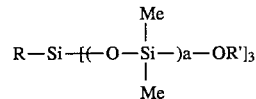

Me is methyl;

R is alkyl having one to ten carbon atoms;

R' is methyl or ethyl;

a is an integer ranging from 4 to 12.

We have surprisingly learned that the value of "a" is critical in developing a product which gives the desired hydrophobicity. The critical range is from 4 to 12. titanium dioxide's value as a pigment is based upon it's ability to remain dispersed and unreacted. Untreated titanium dioxide, placed into water, loses its effectiveness and good aesthetic qualities due to agglomeration. If the value of "a" is too low, the treated titanium dioxide is not sufficiently hydrophobic and it's value as a pigment is destroyed. Making titanium dioxide permanently hydrophobic by treatment with the correct silicone compound is highly desirable and heretofore very difficult to attain.

The compounds of the present invention are hydrophobic titanium dioxide which is prepared by the reaction of a silicone compound conforming to the following structure:

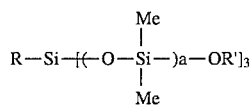

Me is methyl;

R is alkyl having one to ten carbon atoms;

R' is methyl or ethyl;

a is an integer ranging from 4 to 12;

reacted with titanium dioxide.

The hydrophobizing process comprises;

1. contacting titanium dioxide with an effective hydrophobizing concentration of a silicone which conforms to the following structure:

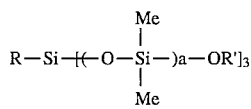

Me is methyl;

R is alkyl having one to ten carbon atoms;

R' is methyl or ethyl;

a is an integer ranging from 4 to 12;

then heating the mixture to a temperature of between 40 C. and 100 C., for two to ten hours.

The product so produced surprisingly is hydrophobic and maintains the desirable performance characteristics making the titanium dioxide useful in many applications including as a sun screen.

While not wishing to be limited to a specific theory of why only specific silicone compounds of the present invention are effective, we believe that the placement of the reactive groups on the molecule have a dramatic affect upon the efficiency of hydrophobization.

The reaction by which hydrophobization occurs is one in which active sites on the titanium dioxide reacts with the silicone to result in a covalent bond between silicone and titanium dioxide, and the formation of R'OH. The reaction is summarized as follows:

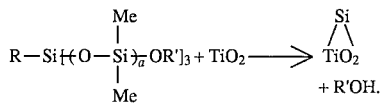

It should be clear from the above that the presence of three R' groups on the silicone compound can result in the formation of a multiple bonds bond between silicone the titanium dioxide crystals. Since no water is present in this process, the titanium dioxide crystals remain intact and "frozen" in shape by the silicone which acts like a matrix for the titanium dioxide crystals. The silicone preserves the structure of the titanium dioxide crystals, eliminates the reactivity in water, and makes them hydrophobic. This allows for the exposure of the hydrophobic titanium dioxide to water without deleterious affect to the titanium dioxide caused by the reactivity of the titanium dioxide in aqueous products. All these improvements are a direct unexpected result of modifying the surface of the titanium dioxide with a specific silicone compound, freezing the structure of the titanium dioxide, hydrophobizing it and removing the undesired reactivity.

When drawn out in it's full structure, it becomes clear that the position of the R' groups can be varied by variation in "a". That is as "a" increases the distance between the R' groups increase and the three dimensional structure changes.

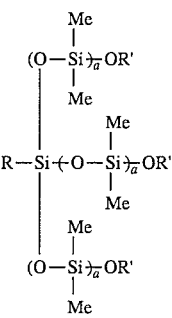

We have learned that the value of "a" is critical to the functionality of the hydrophobizing process. Specifically, "a" is zero, the treated titanium dioxide does not maintain it's structure when exposed to water. There is little affect upon the effectiveness of the hydrophibization until a value of about 4 is reached. The best performance is attained as a approaches 8. As "a" is increased further the silicone molecule becomes more hydrophobic and higher in molecular weight, this limits it's effectiveness in coating the titanium dioxide. In effect the reactive silicone is acting more like an oil than like a hydrophobizing agent, resulting in a titanium dioxide which is not covalently bonded to silicone. A non covalent bond is easily removed by contact with water, resulting in agglomeration of the titanium dioxide, due to reactive groups present in the titanium dioxide, and silicone oil floating on the top of the aqueous formulation.

The production of R'OH as a by product in a dry process, as opposed to s slurry process, is very desirable. Another approach is the use of silicone compounds containing silanic hydrogen compounds of the structure Si—H, results in the evolution of copious amounts of flammable hydrogen gas. In addition the use of these kinds of compounds do not give the desired properties.

PREFERRED EMBODIMENTS

In a preferred embodiment the concentration of silicone compound ranges from 0.1 to 30% by weight.

In another preferred embodiment the concentration of silicone ranges from 0.5 to 20% by weight.

In another preferred embodiment the concentration of silicone ranges from 1.0 to 10.0%.

In a preferred embodiment a is an integer ranging from 6 to 12.

In another preferred embodiment a is an integer ranging from 4 to 8.

In a preferred embodiment R is methyl.

In another preferred embodiment R is octyl.

In another preferred embodiment R is butyl.

In another preferred embodiment R is ethyl.

In a preferred embodiment, the process of the present invention is conducted at a temperature of between 80 and 100 C.

In another preferred embodiment, the process of the present invention is conducted at a temperature of between 90 and 100 C.

EXAMPLES

Silicone Compounds

The silicone compounds useful for the preparation of the compounds of the present invention were provided by Siltech Inc. and conform to the following structures:

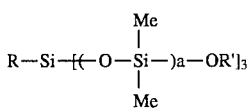

Me is methyl;
R is alkyl having one to ten carbon atoms;
R' is methyl or ethyl;
a is an integer ranging from 4 to 12.

Silicone Compounds Useful for the Present Invention

The following are examples of materials which are compounds useful in treating the titanium dioxide according to our invention;

| Silicone Example | R | R' | a |
|---|---|---|---|
| 1 | $CH_3$ | $CH_3$ | 4 |
| 2 | $CH_3$ | $CH_2CH_3$ | 8 |
| 3 | $CH_3$ | $CH_3$ | 12 |
| 4 | $C_4H_9$ | $CH_3$ | 4 |
| 5 | $C_4H_9$ | $CH_2CH_3$ | 12 |
| 6 | $C_8H_{17}$ | $CH_3$ | 4 |
| 7 | $C_8H_{17}$ | $CH_2CH_3$ | 8 |
| Silicone Compounds Not Useful for the Present Invention (For comparison) | | | |
| 8 | $CH_3$ | $CH_3$ | 0 |
| 9 | $CH_3$ | $CH_2CH_3$ | 2 |
| 10 | $C_4H_9$ | $CH_3$ | 0 |
| 11 | $C_4H_9$ | $CH_2CH_3$ | 2 |

Titanium Dioxide

Titanium dioxide used in the preparation of the compounds of the present invention are commercially available from, SunSmart Inc.

The titanium dioxide used in the preparation of the products in the examples are SunSmart's T-Cote.

Process

The compounds of the present invention are prepared by contacting titanium dioxide with an effective hydrophobizing concentration (generally between 0.1% and 25% by weight of the total formulation) of a silicone which conforms to the following structure:

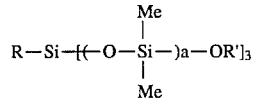

Me is methyl;
R is alkyl having one to ten carbon atoms;
R' is methyl or ethyl;
a is an integer ranging from 4 to 12;
then heating the intermediate to a temperature of between 40 C. and 100 C., for between 2 hr and 10 hr. During this time alcohol is removed. The reaction is considered complete when 97% of the theoretical alcohol is removed. The quantity of alcohol removed is considered more important than the time at which the material is held at temperature.

When R' is CH3, the alcohol removed is methanol. When R' is CH2CH3 the alcohol removed is ethanol.

The titanium dioxide is coated dry. The silicone can be applied by simply mixing it with the titanium dioxide, or in a preferred method using traditional methods for applying liquids to solids like a "V" blender.

Example 12

To 90.0 grams of titanium dioxide is added 10.0 grams of silicone Example #1. The powder is then mixed well. The powder is then placed in an oven and heated to 80 C., for 6 hr. During this time alcohol is removed. The reaction is considered complete when 97% of the theoretical alcohol is removed. The amount of alcohol removed is determined by weighing the contained.

Examples 13–22

Example 12 is repeated only this time the specified amount of the specified silicone is added in place of the 10 grams of silicone Example 1 and the specified number of grams of titanium dioxide are used.

| | Compounds of the Present Invention | |
|---|---|---|
| Example | Silicone Compound Example/Grams | Titanium dioxide Grams |
| 13 | 2     25.0 | 75.0 |
| 14 | 3     1.0 | 99.0 |
| 15 | 4     5.0 | 95.0 |
| 16 | 5     10.0 | 90.0 |
| 17 | 6     0.1 | 99.1 |
| 18 | 7     10.0 | 90.0 |
| 19 | 8     25.0 | 75.0 |
| 20 | 9     1.0 | 99.0 |
| 21 | 10    5.0 | 95.0 |
| 22 | 11    10.0 | 90.0 |

Applications Results (a) Viscosity in Formulations

The viscosity of a dispersion of titanium dioxide in octyl palmitate is also an indication of the effectiveness of the treatment of titanium dioxide. Particles which are effectively treated do not swell in oil. The more the titanium dioxide swells the higher the viscosity of a dispersion.

The following test formula was evaluated;

| % Weight | Material |
|---|---|
| 33.0 | titanium dioxide |
| 67.0 | Octyl Palmitate |
| 100.0 | |

The dispersions were made using a sonic probe 100 watts at 50% power. The viscosity was measured using a Brookfield Viscometer. Again the higher the viscosity, the greater the oil swell and the less efficient the coating.

| Test Material | Viscosity in formulation |
|---|---|
| Example 19 | 440 cps |
| Example 22 | 410 cps |
| Example 21 | 500 cps |
| Untreated $TiO_2$ | 960 cps |

The lower the viscosity, the more effective the surface treatment.

(b) Stability in Aqueous Vitamin C

As noted above, untreated $TiO_2$ will react with an aqueous solution of vitamin C to produce a yellow color. The more intense the color, the greater the reactivity of the $TiO_2$. This offers a good analytical test for effectiveness of the treatment method.

Method 5.0 grams of the test $TiO_2$ is added to 5 grams of a 1% weight/weight solution of vitamin C in water. 0.05 grams of dioctylsulfosuccinate is then added to speed up the wetting of the $TiO_2$. The resultant slurry is mixed with a magnetic stirrer for 10 minutes. 5 grams of a 2% weight/weight solution of xanthan gum in water is added under agitation. This results in a thick slurry which can be drawn into a film on a glass plate. The slurry is drawn down on Form 3NT-3 ink test coat book paper from Leneta Co in Hohokus N.J., using a #22 wire wound dry down bar. The film is allowed to dry 1 hour. The color of the resultant film is measured using an X-rite model 418 reflectance densimeter on the white yellow filter. Four films are cast for each product evaluated.

|  | Untreated $TiO_2$ | Ex. 19 | Ex. 22 | Background |
| --- | --- | --- | --- | --- |
| Test 1 | 0.20 | 0.17 | 0.17 | 0.16 |
| Test 2 | 0.19 | 0.16 | 0.17 | 0.15 |
| Test 3 | 0.21 | 0.17 | 0.16 | 0.15 |
| Test 4 | 0.19 | 0.16 | 0.17 | 0.15 |
| Average | 0.1975 | 0.165 | 0.17 | 0.15 |

The background is subtracted from the measurement for a yellowing measurement.

|  | Untreated $TiO_2$ | Ex. 19 | Ex. 22 |
| --- | --- | --- | --- |
| Average | 0.1975 | 0.165 | 0.17 |
| Ave-Background | 0.0475 | 0.015 | 0.02 |

The untreated is over 3 times more yellow than example 19 and 2 times more yellow than example 22. The reduction in reactivity is a demonstration of the effectiveness of the coating.

The hydrophobized titanium dioxide is used in a variety of applications and formulations. These applications include personal care sun screen applications. The formulations contain titanium dioxide and other ingredients which may include water, inorganic pigments, organic pigments, emulsifiers, oil soluble sun screens, water soluble sun screens, alpha hydroxy acids, dispersants, oil soluble vitamins, water soluble vitamins, waxes and silicone.

We claim:

1. A process for protecting the skin from the ultra violet rays of the sun, which comprises contacting the skin with an effective protecting concentration of a hydrophobic titanium dioxide which is prepared by the reaction of a silicone compound conforming to the following structure:

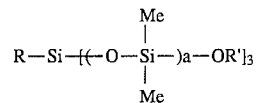

Me is methyl;

R is alkyl having one to ten carbon atoms;

R' is methyl or ethyl;

a is an integer ranging from 4 to 12;

with titanium dioxide.

2. A process of claim 1 wherein said effective protecting concentration ranges between 0.1% and 25% by weight.

3. A process of claim 1 wherein said effective protecting concentration ranges between 0.5% and 20% by weight hydrophobic titanium dioxide.

4. A process of claim 1 wherein said effective protecting concentration ranges between 1.0% and 10% by weight hydrophobic titanium dioxide.

5. A process of claim 1 wherein a is an integer ranging from 6 to 12.

6. A process of claim 1 wherein a is an integer ranging from 4 to 8.

7. A process of claim 1 wherein R is methyl.

8. A process of claim 7 wherein said effective protecting concentration ranges between 0.1% and 25% by weight.

9. A process of claim 7 wherein said effective protecting concentration ranges between 0.5% and 20% by weight hydrophobic titanium dioxide.

10. A process of claim 7 wherein said effective protecting concentration ranges between 1.0% and 10% by weight hydrophobic titanium dioxide.

11. A process of claim 2 wherein R is octyl.

12. A process of claim 11 wherein said effective protecting concentration ranges between 0.1% and 25% by weight.

13. A process of claim 11 wherein said effective protecting concentration ranges between 0.5% and 20% by weight hydrophobic titanium dioxide.

14. A process of claim 11 wherein said effective protecting concentration ranges between 1.0% and 10% by weight hydrophobic titanium dioxide.

15. A process of claim 1 wherein R is isobutyl.

16. A process of claim 15 wherein said effective protecting concentration ranges between 0.1% and 25% by weight.

17. A process of claim 15 wherein said effective protecting concentration ranges between 0.5% and 20% by weight hydrophobic titanium dioxide.

18. A process of claim 15 wherein said effective protecting concentration ranges between 1.0% and 10% by weight hydrophobic titanium dioxide.

19. A process of claim 1 wherein R is ethyl.

20. A process of claim 19 wherein said effective protecting concentration ranges between 0.1% and 25% by weight.

* * * * *